(12) United States Patent
Kim et al.

(10) Patent No.: US 11,572,453 B2
(45) Date of Patent: Feb. 7, 2023

(54) PLASTICIZER COMPOSITION AND RESIN COMPOSITION INCLUDING THE SAME

(71) Applicant: LG CHEM, LTD., Seoul (KR)

(72) Inventors: Hyun Kyu Kim, Daejeon (KR); Mi Yeon Lee, Daejeon (KR); Yun Ki Cho, Daejeon (KR); Jeong Ju Moon, Daejeon (KR); Joo Ho Kim, Daejeon (KR); Seok Ho Jeong, Daejeon (KR)

(73) Assignee: LG CHEM, LTD., Seoul (KR)

( * ) Notice: Subject to any disclaimer, the term of this patent is extended or adjusted under 35 U.S.C. 154(b) by 0 days.

(21) Appl. No.: 15/752,087

(22) PCT Filed: May 17, 2017

(86) PCT No.: PCT/KR2017/005110
§ 371 (c)(1),
(2) Date: Feb. 12, 2018

(87) PCT Pub. No.: WO2017/200293
PCT Pub. Date: Nov. 23, 2017

(65) Prior Publication Data
US 2018/0237613 A1 Aug. 23, 2018

(30) Foreign Application Priority Data

May 18, 2016 (KR) .................. 10-2016-0060831
May 15, 2017 (KR) .................. 10-2017-0059726

(51) Int. Cl.
| | |
|---|---|
| C08K 5/103 | (2006.01) |
| C07C 69/704 | (2006.01) |
| C07C 69/78 | (2006.01) |
| C07C 69/82 | (2006.01) |
| C08K 5/11 | (2006.01) |
| C08K 5/12 | (2006.01) |
| C08K 5/101 | (2006.01) |
| C08L 23/06 | (2006.01) |
| C08L 23/08 | (2006.01) |
| C08L 23/12 | (2006.01) |
| C08L 25/06 | (2006.01) |
| C08L 27/06 | (2006.01) |
| C08L 61/02 | (2006.01) |
| C08L 75/04 | (2006.01) |

(52) U.S. Cl.
CPC ............. *C08K 5/12* (2013.01); *C07C 69/704* (2013.01); *C07C 69/78* (2013.01); *C07C 69/82* (2013.01); *C08K 5/101* (2013.01); *C08K 5/103* (2013.01); *C08K 5/11* (2013.01); *C08L 23/06* (2013.01); *C08L 23/0853* (2013.01); *C08L 23/12* (2013.01); *C08L 25/06* (2013.01); *C08L 27/06* (2013.01); *C08L 61/02* (2013.01); *C08L 75/04* (2013.01)

(58) Field of Classification Search
CPC .......... C08K 5/12; C08K 5/101; C08K 5/103; C08K 5/11; C08L 23/06; C08L 23/0853; C08L 23/12; C08L 25/06; C08L 27/06; C08L 61/02; C08L 75/04; C07C 69/704; C07C 69/78; C07C 69/82
USPC ....................................................... 524/293
See application file for complete search history.

(56) References Cited

U.S. PATENT DOCUMENTS

| | | | |
|---|---|---|---|
| 5,990,214 A * | 11/1999 | Arendt ................... | C07C 69/76 |
| | | | 524/296 |
| 8,372,912 B2 | 2/2013 | Olsen et al. | |
| 9,388,293 B2 | 7/2016 | Olsen et al. | |
| 2007/0037926 A1 | 2/2007 | Olsen et al. | |
| 2010/0305255 A1 | 12/2010 | Grass et al. | |
| 2011/0046283 A1* | 2/2011 | Grass ..................... | C07C 69/704 |
| | | | 524/285 |
| 2011/0281987 A1 | 11/2011 | Godwin et al. | |
| 2013/0137789 A1 | 5/2013 | Olsen et al. | |
| 2013/0274395 A1 | 10/2013 | Arendt et al. | |
| 2013/0274396 A1 | 10/2013 | Arendt et al. | |
| 2013/0310473 A1 | 11/2013 | Becker et al. | |
| 2013/0317152 A1* | 11/2013 | Becker ................ | D06N 7/0002 |
| | | | 524/296 |
| 2013/0317153 A1 | 11/2013 | Grass et al. | |
| 2014/0336320 A1* | 11/2014 | Lee ......................... | C07C 67/03 |
| | | | 524/296 |

(Continued)

FOREIGN PATENT DOCUMENTS

| | | | |
|---|---|---|---|
| CN | 101238175 A | | 8/2008 |
| CN | 101993548 A | * | 3/2011 |

(Continued)

OTHER PUBLICATIONS

KR 10-2013-0067513 A, machine translation, EPO espacenet. (Year: 2013).*

(Continued)

*Primary Examiner* — Michael L Leonard
(74) *Attorney, Agent, or Firm* — Morgan, Lewis & Bockius LLP

(57) ABSTRACT

The present invention relates to a plasticizer composition and a resin composition including the same. The compositions comprise a terephthalate-based material, a dibenzoate-based material, and a citrate. The compositions and methods have a weight ratio of the terephthalate-based material to the benzoate-based material of 99:1 to 1:99. The citrate-based material is included at 1 to 80 parts by weight with respect to 100 parts by weight of the total weight of the terephthalate-based material and the dibenzoate-based material.

14 Claims, No Drawings

(56) References Cited

U.S. PATENT DOCUMENTS

| | | |
|---|---|---|
| 2015/0232411 A1 | 8/2015 | Storzum et al. |
| 2016/0053085 A1 | 2/2016 | Arendt et al. |
| 2016/0159726 A1 | 6/2016 | Storzum et al. |
| 2016/0237243 A1* | 8/2016 | Woldt .................. C07C 67/08 |
| 2016/0326346 A1 | 11/2016 | Gourdin et al. |

FOREIGN PATENT DOCUMENTS

| | | | |
|---|---|---|---|
| CN | 102272215 A | 12/2011 | |
| CN | 103687732 A | 3/2014 | |
| CN | 103756455 A | 4/2014 | |
| CN | 104109324 A * | 10/2014 | ......... B29C 47/0004 |
| EP | 2810932 A1 | 12/2014 | |
| GB | 496574 A * | 12/1938 | |
| KR | 10-2010-0116176 A | 10/2010 | |
| KR | 20130067513 A * | 6/2013 | |
| KR | 10-2013-0119947 A | 11/2013 | |
| KR | 10-2013-00141611 A | 12/2013 | |
| KR | 10-2015-0123346 A | 11/2015 | |
| TW | 201538480 A | 10/2015 | |
| WO | WO-2008140177 A1 * | 11/2008 | ............ C07C 69/82 |
| WO | 2015-101569 A | 7/2015 | |

OTHER PUBLICATIONS

CN 101993548 A, machine translation, EPO espacenet. (Year: 2011).*

Wardzińska et al., "Influence of the Glycol Component in Dibenzoate Plasicizers on the Properties of Plasticized PVC Films," J. Appl. Polym. Sci, vol. 97, No. 3, 822-824. (Year: 2005).*

CN 104109324 A, machine translation, EPO espacenet. (Year: 2014).*

* cited by examiner

PLASTICIZER COMPOSITION AND RESIN COMPOSITION INCLUDING THE SAME

TECHNICAL FIELD

This application is the national stage of International Application No. PCT/KR2017/005110 filed on May 17, 2017, and claims the benefit of Korean Application No. 10-2016-0060831, filed on May 18, 2016 and Korean Patent Application No. 10-2017-0059726, filed on May 15, 2017, all of which are hereby incorporated by reference in their entirety for all purposes as if fully set forth herein.

The present invention relates to a plasticizer composition and a resin composition including the same.

BACKGROUND ART

Conventionally, a plasticizer forms an ester through a reaction between an alcohol and a polycarboxylic acid such as phthalic acid or adipic acid. In addition, in consideration of domestic and international regulations for phthalate-based plasticizers harmful to humans, there is ongoing research on plasticizer compositions that can replace phthalate-based plasticizers such as terephthalate-, trimellitate-, and other polymer-based plasticizers.

Generally, a plasticizer is used as a material for various products such as electric wires, pipes, flooring materials, wallpaper, sheets, artificial leather, tarpaulins, tape and food wrapping materials obtained in the related industries according to processing methods such as extrusion molding, injection molding, calendering, etc. after suitably adding various additives including resins like polyvinyl chloride (PVC), etc., fillers, stabilizers, pigments, anti-fog agents to provide various processing properties.

Meanwhile, there is an increasing demand for environmentally friendly products relating to flooring materials, wallpaper, soft and hard sheets, etc. obtained in the plastisol industry, the calendering industry, the extruding/injecting compound industry, etc., and in order to reinforce quality characteristics, processability and productivity of each end product for such environmentally friendly products, suitable plasticizers have to be used in consideration of discoloration, migration, mechanical properties, etc.

Depending on properties required by industry in various areas of use, such as tensile strength, an elongation rate, light fastness, a migration property, gelability or an absorption rate, a PVC resin is mixed with a supplementary material such as a plasticizer, a filler, a stabilizer, a viscosity depressant, a dispersant, an antifoaming agent or a foaming agent.

In the current plasticizer market, environmentally-friendly plasticizers are competitively developing in the related field due to environmental issues of phthalate plasticizers, and recently, new products for overcoming inferiority of di(2-ethylhexyl)terephthalate (DEHTP) in qualities such as plasticization efficiency, migration, etc., which are being used as general purpose products among such environmentally-friendly plasticizers, have been developed.

Therefore, it is necessary to continue conducting research on technology for developing products with a new composition which has properties superior to those of the DEHTP in order to be optimally applied as a plasticizer for a vinylchloride-based resin.

DISCLOSURE

Technical Problem

Therefore, during research on plasticizers, the inventors developed a plasticizer composition, which can improve inferior properties caused by structural restraints, is environmentally friendly, can be improved in processability due to an improved absorption rate and improved plasticization efficiency, can reduce the total amount of the plasticizer applied due to improved physical properties such as migration and volatile loss, and can have excellent mechanical properties due to improved tensile strength and an improved elongation rate when used in combination with a resin composition, and thus completed the invention.

Technical Solution

In one aspect, the present invention provides a plasticizer composition, which includes a terephthalate-based material; a dibenzoate-based material including one or more dibenzoate-based compounds represented by Formula 1; and a citrate-based material represented by Formula 2. A weight ratio of the terephthalate-based material and the dibenzoate-based material is 99:1 to 1:99, and the citrate-based material is included at 1 to 100 parts by weight with respect to 100 parts by weight of the total weight of the terephthalate-based material and the dibenzoate-based material.

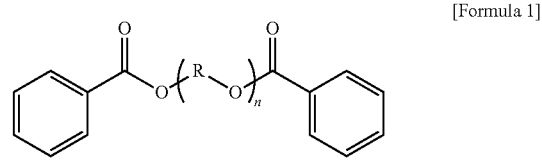

[Formula 1]

In Formula 1, R is a C2 to C4 alkylene group, and n is an integer of 1 to 3.

[Formula 2]

In Formula 2, $R_1$ to $R_3$ are each independently a C4 to C12 alkyl group, and $R_4$ is hydrogen or an acetyl group.

In another aspect, the present invention provides a resin composition which includes 5 to 150 parts by weight of the above-described plasticizer composition with respect to 100 parts by weight of one or more resins selected from the group consisting of ethylene vinyl acetate, polyethylene, polypropylene, polyketone, polyvinyl chloride, polystyrene, polyurethane, and a thermoplastic elastomer.

The resin composition may be applied to manufacture one or more selected from the group consisting of electric wires, flooring materials, interior materials for automobiles, films, sheets, wallpaper and tubes.

Advantageous Effects

A plasticizer composition according to an exemplary embodiment of the present invention can be environmentally friendly, can be improved in processability due to an improved absorption rate and improved plasticization efficiency, can reduce the total amount of the plasticizer applied due to improved physical properties such as migration and volatile loss, and can have excellent mechanical properties due to improved tensile strength and an improved elongation rate when used in a resin composition.

Modes of the Invention

Hereinafter, the present invention will be described in detail.

First, the present invention has a technical feature for providing a plasticizer composition which can improve poor physical properties generated due to its structural restraints.

According to an exemplary embodiment of the present invention, the plasticizer composition includes a terephthalate-based material; a dibenzoate-based material including one or more dibenzoate-based compounds represented by Formula 1 below; and a citrate-based material represented by Formula 2 below, a weight ratio of the terephthalate-based material and the dibenzoate-based material is 99:1 to 1:99, and the citrate-based material is included at 1 to 80 parts by weight with respect to 100 parts by weight of the total weight of the terephthalate-based material and the dibenzoate-based material.

[Formula 1]

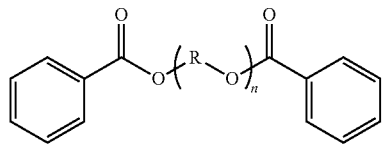

In Formula 1, R is a C2 to C4 alkylene group, and n is an integer of 1 to 3.

[Formula 2]

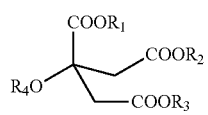

In Formula 2, $R_1$ to $R_3$ are each independently a C4 to C12 alkyl group, and $R_4$ is hydrogen or an acetyl group.

The terephthalate-based material may be a single compound selected from the group consisting of di(2-ethylhexyl) terephthalate (DEHTP), diisononyl terephthalate (DINTP), diisodecyl terephthalate (DIDTP), di(2-propylheptyl)terephthalate (DPHTP), diamyl terephthalate (DATP), dibutyl terephthalate (DBTP), butylisononyl terephthalate (BINTP), butyl(2-ethylhexyl) terephthalate (BEHTP), amylisononyl terephthalate (AINTP), isononyl(2-propylheptyl) terephthalate (INPHTP), amyl(2-propylheptyl) terephthalate (APHTP), amyl(2-ethylhexyl) terephthalate (AEHTP), (2-ethylhexyl)(2-propylheptyl) terephthalate (EHPHTP) and (2-ethylhexyl)isononyl terephthalate (EHINTP), or a mixture of two or more thereof.

In further detail, when the terephthalate-based material is a single compound, the terephthalate-based material may be DEHTP, DINTP, DIDTP, DPHTP, DATP or DBTP, or when the terephthalate-based material is a mixture, 3 types of the terephthalate-based materials may be mixed. For example, the mixture may be a first mixture of DEHTP, BEHTP and DBTP, a second mixture of DINTP, BINTP and DBTP, a third mixture of DEHTP, EHINTP and DINTP, a fourth mixture of DPHTP, INPHTP and DINTP, a fifth mixture of DEHTP, EHPHTP and DPHTP, or a sixth mixture of DATP, AINTP and DINTP.

Particularly, the first to sixth mixtures may have specific composition ratios, the components of each mixture may be mixed at 3.0 to 99.0 mol %; 0.5 to 96.5 mol % and 0.5 to 96.5 mol % as listed in order, respectively.

The composition ratio may be the composition ratio of a mixture generated by esterification, and a desired composition ratio by additionally mixing a specific compound. The composition ratio of a mixture may be regulated suitable for a desired physical property.

In addition, according to an exemplary embodiment of the present invention, a plasticizer composition further including a dibenzoate-based material including one or more dibenzoate-based compounds as well as the terephthalate-based material may be provided. The dibenzoate-based compound may be represented by Formula 1.

[Formula 1]

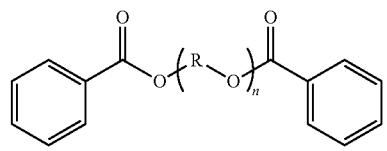

In Formula 1, R is a C2-C4 alkylene group, and n is an integer of 1 to 3.

Specifically, the dibenzoate-based compound represented by Formula 1 may be a compound in which an alkylene group and a dibenzoate group are sequentially bound to either side of an ester group which is present in the center. When n is 2 or more, the alkylene groups represented by R may have the same or different number of carbon atoms. Preferably, the same alkylene groups are bound, they have 2 to 4 carbon atoms, and alkyl groups having 1 to 3 carbon atoms may be bound as a branch. When the branches are bound, the carbon number of the branch is preferably smaller than that of the main chain binding to the dibenzoate group.

Here, when n is 2 or more, and the alkylene groups represented by R are the same, the compound of the present invention may be called a non-hybrid dibenzoate-based compound, whereas when n is 2 or more, and the alkylene groups represented by R are different, the compound of the present invention may be called a hybrid dibenzoate-based compound. However, when used as a plasticizer composition, the non-hybrid dibenzoate-based compound may be more common than the hybrid dibenzoate-based compound, and if there is no mention of hybrid or non-hybrid in the specification, every R may be treated as the same non-hybrid dibenzoate-based compound.

In Formula 1, R is preferably any one selected from the group consisting of ethylene, propylene, isopropylene, butylene and isobutylene, but the present invention is not limited thereto. Preferably, the dibenzoate-based compound represented by Formula 1 is diethylene glycol dibenzoate, dipropylene glycol dibenzoate, or triethylene glycol dibenzoate.

A dibenzoate-based material including one or more such dibenzoate-based compounds may be the diethylene glycol dibenzoate, diisopropylene glycol dibenzoate, triethylene glycol dibenzoate or a mixture thereof, or a mixture further including the dibenzoate-based compound matching the definition of R.

According to an exemplary embodiment of the present invention, the terephthalate-based material and the dibenzoate-based material may be contained in a weight ratio of 99:1 to 1:99 in the plasticizer composition, and the upper limit of the weight ratio range may be 99:1, 95:5, 90:10, 85:15, 80:20, 70:30 or 60:40, and the lower limit thereof may be 1:99, 5:95, 10:90, 15:85, 20:80, 30:70 or 40:60. The range of the weight ratio is preferably 90:10 to 20:80, and more preferably 90:10 to 30:70.

As described in the present invention, when the terephthalate-based material is mixed with the dibenzoate-based material and then applied to a plasticizer composition, the composition may become highly environmentally-friendly, and may be improved in physical properties such as an absorption rate, plasticization efficiency, migration, volatile loss, etc.

According to an exemplary embodiment of the present invention, the plasticizer composition may include the terephthalate-based material and the dibenzoate-based material, and further include a citrate-based material as a third component of the mixture, and the citrate-based material may be represented by Formula 2 below.

[Formula 2]

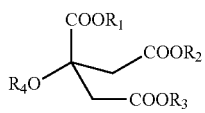

In Formula 2, $R_1$ to $R_3$ are each independently a C4 to C12 alkyl group, and $R_4$ is hydrogen or an acetyl group.

In the citrate-based material of Formula 2, $R_1$ to $R_3$ may be each independently a butyl group, an isobutyl group, a hexyl group, a heptyl group, an isoheptyl group, a 2-ethylhexyl group, an isononyl group, a 2-propylheptyl group, an isodecyl group, an undecyl group or a dodecyl group, and each of $R_1$ to $R_3$ may be the same or different from each other.

However, each of $R_1$ to $R_3$ may have 4 or more and 12 or less carbon atoms, and may be a butyl group, an isobutyl group, an amyl group, a 2-ethylhexyl group, an isononyl group, a 2-propylheptyl group, an isodecyl group, an undecyl group or a dodecyl group.

The citrate in which $R_1$ to $R_3$ are C4 to C12 alkyl groups, which are different from each other, may be, for example, a citrate having a combined substituent of a butyl group and a 2-ethylhexyl group, a citrate having a combined substituent of a butyl group and a heptyl group, a citrate having a combined substituent of an isononyl group and a 2-propylheptyl group, a citrate having a combined substituent of a 2-ethylhexyl group and a 2-propylheptyl group, or a citrate having a combined substituent of an isodecyl group and a 2-ethylhexyl group, or may be a citrate having a combined substituent of two alkyl groups having a different number of carbon atoms selected from 4 to 12. The alkyl group may be linear or branched.

The citrate in which $R_1$ to $R_3$ are C4 to C12 alkyl groups, which are the same as each other, may be, for example, tributylcitrate (TBC), triamylcitrate (TAC), triheptylcitrate (THpC), tri(2-ethylhexyl) citrate (TEHC), triisononyl citrate (TiNC), or tri(2-propylheptyl) citrate (TPHC), or may be any alkyl group having 4 to 12 carbon atoms.

The upper limit of the number of carbon atoms of the alkyl group may be 12. If the citrate has more than 12 carbon atoms, there are concerns about degradation of the absorption rate and the plasticization efficiency due to an excessive increase in molecular weight.

In some cases, in Formula 2, $R_1$ to $R_3$ preferably have 4 to 10 carbon atoms, 4 to 9 carbon atoms, or 4 to 8 carbon atoms.

Meanwhile, a trialkyl citrate or dnalkyl''')(alkyl''') citrate such as the hybrid or non-hybrid alkyl-substituted citrate compound may be applied, and when there is an acetyl group present in the citrate-based plasticizer, that is, $R_4$ is an acetyl group, the physical properties, particularly, processability caused by reduced plasticization efficiency and gelability, of the plasticizer may be reduced in a certain extent. In addition, there may be economic burden and equipment costs for treating wasted acetic acid generated as a byproduct during the preparation.

In other words, when, in the citrate-based plasticizer of Formula 2, $R_4$ is an acetyl group, compared to hydrogen, a decrease in plasticization efficiency, addition of an increased amount of the plasticizer to overcome the decreased plasticization efficiency, and an increase in production cost thereby may occur, and when a citrate-based material in which R7 is an acetyl group is applied, it is necessary to consider various aspects such as marketability, economic feasibility, physical properties, etc.

Such a citrate-based material may be included at 1 to 80 parts by weight, preferably, 3 to 80 parts by weight, and more preferably, 5 to 50 parts by weight with respect to 100 parts by weight of the total weight of a mixture of the terephthalate-based material and the dibenzoate-based material.

When the citrate-based material is contained in the above-described range, low characteristics such as volatile loss and migration loss may be greatly improved without a decrease in plasticization efficiency, and therefore a plasticizer composition having excellent processability and improved physical properties may be provided.

In the present invention, to prepare the plasticizer composition, a blending method may be applied as follows.

A terephthalate-based material and a dibenzoate-based material are prepared, and blended in a specific weight ratio of the terephthalate-based material and the dibenzoate-based material, such as 1:99 to 99:1, thereby preparing the plasticizer composition, and the terephthalate-based material and the dibenzoate-based material may be present in a single compound or a mixture thereof.

When the terephthalate-based material is present in a single compound, a terephthalate-based material may be prepared by direct esterification between any one alcohol selected from the group consisting of 2-ethylhexyl alcohol, isononyl alcohol, 2-propylheptyl alcohol, amyl alcohol, butyl alcohol and isobutyl alcohol, and terephthalic acid.

The direct esterification may be performed by adding terephthalic acid to an alcohol and then reacting the resulting mixture in the presence of a catalyst under a nitrogen atmosphere; removing an unreacted alcohol and neutralizing an unreacted acid; and performing dehydration and filtration through vacuum distillation.

The alcohol may be used in the range of 150 to 500 mol %, 200 to 400 mol %, 200 to 350 mol %, 250 to 400 mol %, or 270 to 330 mol % on the basis of 100 mol % of terephthalic acid.

The catalyst may include, for example, one or more selected from acidic catalysts such as sulfuric acid, hydrochloric acid, phosphoric acid, nitric acid, para-toluenesulfonic acid, methanesulfonic acid, ethanesulfonic acid, propanesulfonic acid, butanesulfonic acid, alkyl sulfate, etc., metal salts such as aluminum sulfate, lithium fluoride, potassium chloride, cesium chloride, calcium chloride, iron chloride, aluminum phosphate, etc., metal oxides such as a heteropolyacid, etc., natural/synthetic zeolites, cation and anion exchange resins, and organic metals such as a tetra alkyl titanate and polymers thereof, etc. As a specific example, the catalyst may be a tetra alkyl titanate.

An amount of the catalyst used may depend on its type, and for instance, the amount of a homogeneous catalyst may be in the range of 0.01 to 5 wt %, 0.01 to 3 wt %, 1 to 5 wt % or 2 to 4 wt % with respect to total 100 wt % of the reactants, and the amount of a heterogeneous catalyst may be in the range of 5 to 200 wt %, 5 to 100 wt %, 20 to 200 wt %, or 20 to 150 wt % with respect to a total amount of the reactants.

Here, the reaction temperature may be 180 to 280° C., 200 to 250° C., or 210 to 230° C.

Meanwhile, to prepare the terephthalate as a single compound, the following transesterification may be used. For example, when dimethyl terephthalate is transesterified with the above-described alcohols, for example, isononyl alcohol, DINTP may be prepared with a yield of 98% or more.

When the terephthalate-based material is a mixture, terephthalate compounds may be prepared through the above-described direct esterification and then mixed, or may be prepared by adding two or more types of alcohol to perform the direct esterification.

In addition, when the terephthalate-based material is a mixture, a terephthalate compound may be prepared by transesterification between any one terephthalate compound selected from DEHTP, DPHTP and DINTP and any one alcohol selected from butyl alcohol, isobutyl alcohol, amyl alcohol, 2-ethylhexyl alcohol, isononyl alcohol and 2-propylheptyl alcohol.

The "transesterification" used herein refers to a reaction between an alcohol and an ester as shown in Reaction Scheme 1, thereby interchanging R" of the ester and R' of the alcohol as shown in Reaction Scheme 1:

[Reaction Scheme 1]

According to an exemplary embodiment of the present invention, the transesterification may produce three types of ester compositions according to three cases in which an alkoxide of the alcohol attacks carbons of two ester (RCOOR") groups present in an ester-based compound; an alkoxide of the alcohol attacks carbons of one ester (RCOOR") group present in an ester-based compound; and there is no reaction between an alcohol and an ester group in an ester-based compound.

In addition, compared to an acid-alcohol esterification, the transesterification does not cause water contamination, may solve problems caused by the use of an acidic catalyst because of proceeding without a catalyst.

For example, through the transesterification between DEHTP and butyl alcohol, a mixture of DEHTP, BEHTP and DBTP may be generated, and the three types of terephthalates may be formed at 3.0 to 70 wt %, 0.5 to 50 wt % and 0.5 to 85 wt %, and particularly, 10 to 50 wt %, 0.5 to 50 wt % and 35 to 80 wt %, respectively, with respect to the total weight of the mixture. Within the above ranges, a terephthalate-based material (mixture) having high process efficiency and excellent processability and absorption rate may be obtained.

In addition, the mixture prepared by the transesterification may be controlled in the composition ratio of the mixture according to the amount of an alcohol to be added.

The amount of an alcohol used herein may be 0.1 to 89.9 parts by weight, preferably, 3 to 50 parts by weight, and more preferably 5 to 40 parts by weight with respect to 100 parts by weight of the terephthalate compound.

As the amount of an alcohol used herein increases, the mole fraction of the terephthalate compound participating in the transesterification also increases. Thus, the contents of products such as two terephthalate compounds in the mixture may increase, and accordingly, the content of the unreacted terephthalate compounds may be likely to be reduced.

According to an exemplary embodiment of the present invention, a molar ratio of the reactants, such as the terephthalate compound and the alcohol, is 1:0.005 to 5.0, 1:0.05 to 2.5, or 1:0.1 to 1.0, and in this range, an ester-based plasticizer composition having high process efficiency and an excellent processability improving effect may be obtained.

However, a composition ratio of the mixture of the three types of terephthalate-based materials is not limited in the above range, and any one of the three types of terephthalates may be further added to change the composition ratio. Available composition ratios of the mixture are as described above.

According to an exemplary embodiment of the present invention, the transesterification may be performed at a reaction temperature of 120 to 190° C., preferably 135 to 180° C., and more preferably 141 to 179° C. for 10 minutes to 10 hours, preferably 30 minutes to 8 hours, and more preferably 1 to 6 hours. Within the temperature and time ranges, a mixture of the terephthalate-based materials at a desired composition ratio may be effectively obtained. Here, the reaction time may be calculated from the time to reach the reaction time after the reactants are increased in temperature.

The transesterification may be performed under an acid catalyst or a metal catalyst, and in this case, has an effect of reducing the reaction time.

The acid catalyst may be, for example, sulfonic acid, methane sulfonate or p-toluene sulfonate, and the metal catalyst may be, for example, an organic metal catalyst, a metal oxide catalyst, a metal salt catalyst or a metal itself.

The metal component may be, for example, any one selected from the group consisting of tin, titanium and zirconium or a mixture of two or more thereof.

In addition, after the transesterification, removing of an unreacted alcohol and a byproduct, such as an ester-based compound represented by Formula 3, by distillation may be further performed.

The distillation may be, for example, two-step distillation for separating the alcohol and the reaction byproducts using the difference in boiling point.

As another example, the distillation may be combined distillation. In this case, an ester-based plasticizer composition can relatively be stably obtained at a desired composition ratio. The combined distillation refers to concurrent distillation of a butanol and reaction byproducts.

The direct esterification and the transesterification may also be applied in preparation of the above-described dibenzoate-based material and citrate-based material. As such, when the dibenzoate-based material and the citrate-based material are prepared by direct esterification or transesterification, the same procedures and details as used in the preparation of the terephthalate-based material may be applied.

The plasticizer composition prepared as described above may be included in a range of 5 to 150 parts by weight, 40 to 100 parts by weight, or 5 to 50 parts by weight with respect to 100 parts by weight of a resin selected from the group consisting of ethylene vinyl acetate, polyethylene, polypropylene, polyketone, polyvinyl chloride, polystyrene, polyurethane, and a thermoplastic elastomer, and thus may be applied as a resin composition effective in all of extrusion/injection molding, and compound, calendering, sheet, and plastisol formulations.

For example, the plasticizer composition may be applied to manufacture electric wires, flooring materials, interior materials for automobiles, films, sheets, wall paper or tubes.

EXAMPLES

Hereinafter, to explain the present invention in detail, the present invention will be described in detail with reference to examples. However, examples according to the present invention may be modified in a variety of different forms, and the scope of the present invention should not be construed as being limited to the examples to be described below. The exemplary embodiments of the present invention are provided for those of ordinary skill in the art to more fully understand the present invention.

Preparation Example 1: Preparation of di(2-ethylhexyl)terephthalate 498.0 g of purified terephthalic acid (TPA), 1,170 g of 2-ethylhexyl alcohol (2-EH; a molar ratio of TPA: 2-EH—(1.0):(3.0)), and 1.54 g of a titanium-based catalyst (tetra isopropyl titanate (TIPT); 0.31 parts by weight with respect to 100 parts by weight of TPA) as a catalyst were added to a 4-neck 3 L reaction vessel equipped with a cooler, a condenser, a decanter, a reflux pump, a temperature controller, an agitator, etc., and a temperature was slowly increased to approximately 170° C. At approximately 170° C., water was generated, and esterification was performed for approximately 4.5 hours while a nitrogen gas was continuously added at a reaction temperature of approximately 220° C. under atmospheric pressure, and then terminated when an acid value reached 0.01.

After the reaction was completed, distillation extraction was performed for 0.5 to 4 hours under reduced pressure to remove unreacted components. To remove unreacted components at a predetermined content or less, steam extraction was performed using steam for 0.5 to 3 hours under reduced pressure, and neutralization was performed using an alkali solution after a reaction solution was cooled to approximately 90° C. Additionally, washing could be performed, and then the reaction solution was dehydrated to remove moisture. Filter media were input to the dehydrated reaction solution, stirred for a predetermined time and then filtered, thereby finally obtaining 1,326.7 g of DEHTP (yield: 99.0%).

Preparation Example 2: Preparation of Diisononyl Terephthalate

DINTP was finally obtained using isononyl alcohol, instead of 2-ethylhexanol used in Preparation Example 1.

Preparation Example 3: Preparation of Dibutyl Terephthalate

DBTP was finally obtained using butanol, instead of 2-ethylhexanol used in Preparation Example 1.

Preparation Example 4: Preparation of TP Mixture of DEHTP/BEHTP/DBTP 2,000 g of DEHTP obtained in Preparation Example 1 and 340 g of n-butanol (17 parts by weight on the basis of 100 parts by weight of DEHTP) were input to a reaction vessel equipped with an agitator, a condensor and a decanter, and allowed to transesterification for 2 hours at a reaction temperature of 160° C. under a nitrogen atmosphere, thereby obtaining a composition including DBTP, butyl(2-ethylhexyl) terephthalate (BEHTP) and DEHTP at 4.0 wt %, 35.0 wt % and 61.0 wt %, respectively.

The reaction product was mixed and distilled to remove butanol and 2-ethylhexyl alcohol, thereby finally preparing a first mixture.

Preparation Example 5: Preparation of TP Mixture of DINTP/EHINTP/DEHTP

A composition including DINTP, (2-ethylhexyl)isononyl terephthalate (EHINTP) and DEHTP at 2.5 wt %, 30.5 wt % and 67.0 wt %, respectively, was obtained using diisononyl terephthalate and 2-ethylhexanol, instead of DEHTP and n-butanol used in Preparation Example 4.

Preparation Example 6: Preparation of TP Mixture of DINTP/EHINTP/DEHTP

A composition including di(2-propylheptyl)terephthalate (DINTP), isononyl(2-propylheptyl)terephthalate (INPHTP) and DINTP at 2.7 wt %, 31.0 wt % and 66.3 wt %, respectively, was obtained using DPHTP and isononyl alcohol, instead of DEHTP and n-butanol used in Preparation Example 4.

Preparation Example 7: Preparation of DEGDB 1,221 g of purified benzoic acid (BA) and 530.5 g of diethylene glycol (DEG) were added at a molar ratio of BA:DEG (2.0):(1.0), and 2.0 g of a titanium-based catalyst (tetraisopropyltitanate (TIPT)) as a catalyst and a small amount of xylene were added to a 4-neck 2 L reaction vessel equipped with a cooler, a condenser, a decanter, a reflux pump, a temperature controller, an agitator, etc., and then a temperature was slowly elevated to approximately 170° C. When water was generated at approximately 170° C., the amount of xylene was adjusted to facilitate the removal of the generated water, and the reaction was terminated when the content of a monobenzoate as an intermediate among the reactants was 5% or less. Afterward, 1,530 g of the final product DEGDB (yield: 98%) was obtained by a method similar to that described in Preparation Example 1.

Preparation Example 8: Preparation of TBC 706 g of TBC (yield: 98%) was finally obtained using 384 g of citric acid and 580 g of butanol as reactants.

Preparation Example 9: Preparation of TOC 1,029 g of TOC (yield: 98%) was finally obtained using 384 g of citric acid and 1,014 g of 2-ethylhexanol as reactants.

Preparation Example 10: Preparation of TiNC 1,111 g of TiNC (yield: 98%) was finally obtained using 384 g of citric acid and 1,123 g of isononanol as reactants.

Preparation Example 11: Preparation of BOC253

840 g of BOC was finally obtained by performing trans-esterification using 1,000 g of TOC prepared in Preparation Example 9 and 300 g of n-butanol as reactants.

The mixture included approximately 20.9 wt % of the combination of three materials including approximately 2.2 wt % of TBC and approximately 18.7 wt % of two types of citrates in which two 2-ethylhexyl groups were replaced by butyl groups, approximately 45.4 wt % of the combination of two types of citrates in which one 2-ethylhexyl group is replaced by a butyl group, and approximately 33.7 wt % of TOC at a weight ratio of approximately 2:5:3 in order of molecular weight.

Examples 1 to 12 and Comparative Examples 1 to 5

Examples and Comparative Examples were prepared using the materials prepared in Preparation Examples 1 to 11 and commercially-available materials as shown in Tables 1 to 3 below. Parts by weight of the citrates shown below are values relative to 100 parts by weight of the total weight of the mixture of a TP-based material and a dibenzoate-based material.

TABLE 1

| | TP-based material | Dibenzoate-based material | Mixed ratio | Citrate (parts by weight) |
|---|---|---|---|---|
| Example 1 | DEHTP | DEGDB | 7:3 | TBC(10) |
| Example 2 | DINTP | DEGDB | 8:2 | TBC(10) |
| Example 3 | DEHTP/BEHTP/DBTP | DEGDB | 6:4 | TBC(10) |
| Example 4 | DPHTP/INPHTP/DINTP | DPGDB | 5:5 | TBC(20) |
| Example 5 | DEHTP | DPGDB | 8:2 | TBC(50) |
| Example 6 | DINTP | TEGDB | 7:3 | TBC(25) |
| Example 7 | DEHTP | DEGDB | 7:3 | TBC(50) |
| Example 8 | DEHTP | DEGDB | 7:3 | TBC(75) |

*GL300 ™: DEHTP produced by LG Chem Ltd.

TABLE 2

| | TP-based material | Dibenzoate-based material | Mixed ratio | Citrate (parts by weight) |
|---|---|---|---|---|
| Example 9 | DEHTP | DEGDB | 5:5 | TOC(20) |
| Example 10 | DINTP/OINTP/DOTP | DEGDB | 6:4 | BOC(10) |
| Example 11 | DEHTP | DPGDB | 6:4 | TOC(25) |
| Example 12 | DINTP | DPGDB | 5:5 | TOC(50) |

*GL300 ™: DEHTP produced by LG Chem Ltd.

TABLE 3

| | TP-based material | Dibenzoate-based material | Mixed ratio | Citrate (parts by weight) |
|---|---|---|---|---|
| Comparative Example 1 | GL300* | | | |
| Comparative Example 2 | DEHTP | DEGDB | 75:25 | |
| Comparative Example 3 | DBTP | DEGDB | 6:4 | |
| Comparative Example 4 | DEHTP | DEGDB | 8:2 | TINC(100) |
| Comparative Example 5 | DEHTP | DPGDB | 7:3 | TBC(100) |

*GL300 ™: DEHTP produced by LG Chem Ltd.

Experimental Example 1: Preparation of Samples and Performance Evaluation 1

Plasticizers of Examples 1 to 8 and Comparative Examples 1 to 3 and 5 were used as experimental samples. For sample preparation, referring to ASTM D638, 40 parts by weight of a plasticizer and 3 parts by weight of a stabilizer (LOX 912 NP) were mixed with 100 parts by weight of PVC in a mixer, and the resulting mixture was subjected to roll-milling at 170° C. for 4 minutes and pressed for 2.5 minutes (low pressure) and 2 minutes (high pressure) at 180° C., thereby manufacturing 1 T and 3 T sheets. Each sample was subjected to a test for physical properties, and the results are shown in Table 4 below.

<Test Items>

Hardness

According to ASTM D2240, Shore hardness (Shore "D") was measured at 25° C. under conditions of 3 T and 10 s.

Tensile Strength

According to ASTM D638, each specimen was pulled at a cross head speed of 200 mm/min (1 T) using a tester, U.T.M, (Manufacturer; Instron, Model No.; 4466), and a position at which the specimen was broken was detected. A tensile strength was calculated as follows:

Tensile strength ($kgf/mm^2$)=Load value (kgf)/Thickness (mm)×Width (mm)

Measurement of Elongation Rate

According to ASTM D638, each specimen was pulled at a cross head speed of 200 mm/min (1 T) using the U.T.M, and a position at which the specimen was broken was detected. An elongation rate was calculated as follows:

Elongation rate (%)=Length after elongation/Initial length×100

Measurement of Migration Loss

An experimental specimen having a thickness of 2 mm or more was obtained according to KSM-3156, and following attachment of glass plates to both sides of the specimen, a weight of 1 $kgf/cm^2$ was applied to the specimen. The specimen was put in a forced convection oven (80° C.) for 72 hours, and cooled at room temperature for 4 hours. Then, after the glass plates attached to both sides of the specimen were removed, a weight was measured before and after the glass plate and the specimen plate were put in the oven and thus a migration loss was calculated by the equation as follows.

Migration loss (%)=[(Initial weight of specimen at room temperature−Weight of specimen after being put into oven)/Initial weight of specimen at room temperature]×100

Measurement of Volatile Loss

The prepared specimen was processed at 100° C. for 72 hours, and a weight of the specimen was measured as follows:

Volatile loss (wt %)=[(Weight of initial specimen−
Weight of specimen after processed at 100° C.
for 72 hours)/Weight of initial specimen]×100

Measurement of Absorption Rate

An absorption rate was evaluated by measuring the time taken to stabilize the torque of a mixer in which a resin and an ester compound are mixed together using a planetary mixer (Brabender, P600) at 77° C. and 60 rpm.

TABLE 4

|  | Hardness (Shore D) | Tensile strength (kg/cm$^2$) | Elongation (%) | Migration loss (%) | Volatile loss (%) | Absorption rate (m:s) |
| --- | --- | --- | --- | --- | --- | --- |
| Example 1 | 48.0 | 285.6 | 311.2 | 1.32 | 1.10 | 4:56 |
| Example 2 | 48.1 | 288.1 | 310.5 | 1.68 | 0.98 | 5:22 |
| Example 3 | 46.0 | 285.1 | 325.4 | 0.58 | 1.20 | 4:33 |
| Example 4 | 47.6 | 275.4 | 298.5 | 1.88 | 1.17 | 4:15 |
| Example 5 | 44.0 | 254.7 | 288.6 | 2.55 | 3.04 | 3:50 |
| Example 6 | 46.3 | 260.8 | 280.9 | 1.70 | 2.40 | 4:18 |
| Example 7 | 43.5 | 268.7 | 293.4 | 2.60 | 2.68 | 4:05 |
| Example 8 | 42.4 | 248.0 | 245.5 | 3.70 | 3.20 | 3:38 |
| Comparative Example 1 | 48.9 | 236.7 | 288.6 | 3.21 | 1.63 | 7:15 |
| Comparative Example 2 | 48.8 | 237.5 | 293.5 | 2.87 | 2.23 | 5:20 |
| Comparative Example 3 | 45.5 | 204.5 | 256.0 | 5.20 | 11.20 | 2:10 |
| Comparative Example 5 | 41.0 | 235.4 | 230.5 | 5.80 | 17.50 | 1:35 |

Referring to Table 4, when Comparative Examples 2 and 3 which had no citrate, Comparative Example 5 which had an excessive citrate, and Comparative Example 1 which has been used as a conventional plasticizer, but was in need of improvement in absorption rate, migration, tensile strength or plasticization efficiency (hardness) are compared to Examples 1 to 8, it can be confirmed that Comparative Example 1 is inferior in tensile strength to the Examples as expected, and since an absorption rate is also longer than 7 minutes and thus a processing time is excessively long, the tensile strength or the elongation rate is very low, and the plasticization efficiency is reduced, it can be estimated that there is chance to have problems in processability and productivity, and an increase in production cost.

In addition, it can be confirmed that, since Comparative Example 2 has neither particularly excellent nor good physical properties, it may be difficult to be commercialized even for a use suitable for a certain property, and Comparative Example 3 may have problems in processability due to an ultimately low tensile strength, low migration loss and low volatile loss, and a very high absorption rate.

In addition, it can be seen that Comparative Example 5 has very low volatile loss and very low migration loss because the citrate is excessively added at more than 80 parts by weight up to 100 parts by weight, and also has problems in processability due to a high absorption rate.

On the other hand, the plasticizers of Examples 1 to 8 have basic levels of mechanical properties, and also exhibit considerable levels of physical properties such as volatile loss and migration loss. Therefore, it can be seen that, when used at the same amount, they can control migration loss in a suitable range with smaller amounts than that of a plasticizer having high migration loss, and also can be confirmed that they may not have problems in processing because of overall similar absorption rates. In addition, it can be confirmed that the Examples having a little lower tensile strength or a little lower elongation rate have low hardness, which can be compensated by plasticization efficiency.

Experimental Example 2: Preparation of Samples and Performance Evaluation 2

The plasticizers of Examples 9 to 12 and Comparative Examples 1 to 4 were used as experimental samples. The preparation of samples and the evaluation of physical properties were carried out as described in Experimental Example 1, and the results are shown in Table 5 below.

TABLE 5

|  | Hardness (Shore D) | Tensile strength (kg/cm$^2$) | Elongation rate (%) | Migration loss (%) | Volatile loss (%) | Absorption rate (m:s) |
| --- | --- | --- | --- | --- | --- | --- |
| Example 9 | 48.5 | 295.1 | 315.0 | 1.02 | 0.75 | 5:55 |
| Example 10 | 48.2 | 290.5 | 304.7 | 1.42 | 0.95 | 5:08 |
| Example 11 | 47.2 | 298.7 | 302.5 | 0.77 | 0.60 | 5:05 |
| Example 12 | 49.0 | 317.0 | 308.5 | 0.50 | 0.72 | 6:44 |
| Comparative Example 1 | 48.9 | 236.7 | 288.6 | 3.21 | 1.63 | 7:15 |
| Comparative Example 2 | 48.8 | 237.5 | 293.5 | 2.87 | 2.23 | 5:20 |
| Comparative Example 3 | 45.5 | 204.5 | 256.0 | 5.20 | 11.20 | 2:10 |
| Comparative Example 4 | 50.3 | 265.4 | 245.0 | 2.50 | 1.08 | 9:25 |

Referring to Table 5, when Comparative Examples 2 and 3 which had no citrate, Comparative Example 4 which had an excessive citrate, and Comparative Example 1 which has been used as a conventional plasticizer, but was in need of improvement in absorption rate, migration, tensile strength or elongation rate are compared to Examples 9 to 12, it can be confirmed that, in Comparative Example 1, as expected, all of the physical properties such as tensile strength, an elongation rate, migration loss and volatile loss are in low levels and a hardness is high, and therefore it is difficult to compensate these disadvantages by plasticization efficiency.

In addition, it can be confirmed that Comparative Example 2 has physical properties which are neither particularly excellent nor high, and therefore can be difficult to be commercialized even for a use suitable for a certain property, and Comparative Example 3 may have excellent plasticization efficiency, ultimately low tensile strength and considerably low migration loss and volatile loss, and also have a high absorption rate, thereby causing problems in processability.

In addition, it can be seen that, since Comparative Example 4 has excessively high hardness, although having lower plasticization efficiency, it is considerably decreased in the tensile strength and the elongation rate, compared to the Examples. It can also be confirmed that Comparative Example 4 has a considerably lower absorption rate, and therefore has a serious effect on processability in conjunction with the plasticization efficiency.

On the other hand, the plasticizers of Examples 9 to 12 has basically excellent mechanical properties such as tensile strength and an elongation rate, and favorable physical properties such as volatile loss and migration loss. Therefore, it can be seen that, when used at the same amount, these plasticizers can control the migration loss in a suitable range with a lower amount than that of a plasticizer having high migration loss, and also can be confirmed that they have satisfactory absorption rate and hardness, and excellent processability.

Accordingly, referring to Tables 4 and 5, when a terephthalate-based material and a dibenzoate-based material are used as plasticizers as well as a citrate-based material, it can be confirmed that the migration loss and the volatile loss, as well as the mechanical properties, can be reduced, and processability can be controlled at an excellent level, and it can be seen that the physical properties can be controlled by adjusting the number of carbon atoms of the citrate to a suitable level.

The invention claimed is:

1. A plasticizer composition, comprising:
   a terephthalate-based material; a dibenzoate-based material including a dibenzoate-based compound; and a citrate-based material,
   wherein a weight ratio of the terephthalate-based material and the dibenzoate-based material is 80:20 to 50:50, and
   the citrate-based material is included at 20 to 80 parts by weight with respect to 100 parts by weight of the total weight of the terephthalate-based material and the dibenzoate-based material, and is selected from the group consisting of tributyl citrate (TBC), trioctyl citrate (TOC), triheptyl citrate (THpC), tri(2-ethylhexyl)citrate (TEHC), triisononyl citrate (TiNC), and tri(2-propylheptyl) citrate (TPHC):
   wherein the terephthalate-based material is one or more selected from the group consisting of di(2-ethylhexyl) terephthalate (DEHTP), diisononyl terephthalate (DINTP), diisodecyl terephthalate (DIDTP), di(2-propylheptyl)terephthalate (DPHTP), diamyl terephthalate (DATP), dibutyl terephthalate (DBTP), butylisononyl terephthalate (BINTP), butyl(2-ethylhexyl) terephthalate (BEHTP), amylisononyl terephthalate (AINTP), isononyl(2-propylheptyl) terephthalate (INPHTP), amyl(2-propylheptyl) terephthalate (APHTP), amyl(2-ethylhexyl) terephthalate (AEHTP), (2-ethylhexyl)(2-propylheptyl) terephthalate (EHPHTP) and (2-ethylhexyl)isononyl terephthalate (EHINTP), and
   wherein the dibenzoate-based compound is diethylene glycol dibenzoate (DEGDB), and DEGDB is the only dibenzoate included in the plasticizer composition.

2. The plasticizer composition of claim 1, wherein the terephthalate-based material is any one selected from the group consisting of di(2-ethylhexyl)terephthalate (DEHTP), diisononyl terephthalate (DINTP), diisodecyl terephthalate (DIDTP), di(2-propylheptyl)terephthalate (DPHTP), diamyl terephthalate (DATP) and dibutyl terephthalate (DBTP).

3. The plasticizer composition of claim 1, wherein the terephthalate-based material is
   a first mixture of di(2-ethylhexyl)terephthalate (DEHTP), butyl(2-ethylhexyl) terephthalate (BEHTP) and dibutyl terephthalate (DBTP),
   a second mixture of diisononyl terephthalate (DINTP), butylisononyl terephthalate (BINTP) and dibutyl terephthalate (DBTP),
   a third mixture of di(2-ethylhexyl)terephthalate (DEHTP), (2-ethylhexyl)isononyl terephthalate (EHINTP) and diisononyl terephthalate (DINTP),
   a fourth mixture of di(2-propylheptyl)terephthalate (DPHTP), isononyl(2-propylheptyl) terephthalate (INPHTP) and diisononyl terephthalate (DINTP),
   a fifth mixture of di(2-ethylhexyl)terephthalate (DEHTP), (2-ethylhexyl)(2-propylheptyl) terephthalate (EHPHTP) and di(2-propylheptyl)terephthalate (DPHTP), or
   a sixth mixture of diamy terephthalate (DATP), amylisononyl terephthalate (AINTP) and diisononyl terephthalate (DINTP).

4. A resin composition, comprising:
   100 parts by weight of a polyvinyl chloride; and 5 to 150 parts by weight of the plasticizer composition of claim 1.

5. The resin composition of claim 4, wherein the resin composition is applied to manufacture one or more selected from the group consisting of electric wires, flooring materials, interior materials for automobiles, films, sheets, wall paper and tubes.

6. The plasticizer composition of claim 1, wherein the terephthalate-based material is a first mixture of di(2-ethylhexyl)terephthalate (DEHTP), butyl(2 -ethylhexyl) terephthalate (BEHTP) and dibutyl terephthalate (DBTP).

7. The plasticizer composition of claim 1, wherein the terephthalate-based material is a second mixture of diisononyl terephthalate (DINTP), butylisononyl terephthalate (BINTP) and dibutyl terephthalate (DBTP).

8. The plasticizer composition of claim 1, wherein the terephthalate-based material is a third mixture of di(2-ethylhexyl)terephthalate (DEHTP), (2-ethylhexyl)isononyl terephthalate (EHINTP) and diisononyl terephthalate (DINTP).

9. The plasticizer composition of claim 1, wherein the terephthalate-based material is a fourth mixture of di(2-propylheptyl)terephthalate (DPHTP), isononyl(2-propylheptyl) terephthalate (INPHTP) and diisononyl terephthalate (DINTP).

10. The plasticizer composition of claim 1, wherein the terephthalate-based material is a fifth mixture of di(2-ethylhexyl)terephthalate (DEHTP), (2-ethylhexyl)(2-propylheptyl) terephthalate (EHPHTP) and di(2-propylheptyl)terephthalate (DPHTP).

11. The plasticizer composition of claim 1, wherein the terephthalate-based material is a sixth mixture of diamyl terephthalate (DATP), amylisononyl terephthalate (AINTP) and diisononyl terephthalate (DINTP).

12. The plasticizer composition of claim 1, wherein the terephthalate-based material is one or more selected from the group consisting of: diisodecyl terephthalate (DIDTP), di(2-propylheptyl)terephthalate (DPHTP), diamyl terephthalate (DATP), butylisononyl terephthalate (BINTP), butyl (2-ethylhexyl) terephthalate (BEHTP), amylisononyl terephthalate (AINTP), isononyl(2-propylheptyl) terephthalate (INPHTP), amyl(2-propylheptyl) terephthalate (APHTP), amyl(2-ethylhexyl) terephthalate (AEHTP), (2-ethylhexyl) (2-propylheptyl)terephthalate (EHPHTP) and (2-ethylhexyl) isononyl terephthalate (EHINTP).

13. A plasticizer composition, comprising:
a terephthalate-based material; a dibenzoate-based material including a dibenzoate-based compound; and a citrate-based material,
wherein a weight ratio of the terephthalate-based material and the dibenzoate-based material is 80:20 to 50:50, and
the citrate-based material is included at 20 to 80 parts by weight with respect to 100 parts by weight of the total weight of the terephthalate-based material and the dibenzoate-based material, and is tributyl citrate (TBC):
wherein the terephthalate-based material comprises di(2-ethylhexyl)terephthalate (DEHTP), and
wherein the dibenzoate-based compound is diethylene glycol dibenzoate (DEGDB), and DEGDB is the only the dibenzoate-based compound included in the plasticizer composition.

14. A plasticizer composition, comprising:
a terephthalate-based material; a dibenzoate-based material including a dibenzoate-based compound; and a citrate-based material,
wherein a weight ratio of the terephthalate-based material and the dibenzoate-based material is 80:20 to 50:50, and
the citrate-based material is included at 20 to 80 parts by weight with respect to 100 parts by weight of the total weight of the terephthalate-based material and the dibenzoate-based material, and is selected from the group consisting of tributyl citrate (TBC), trioctyl citrate (TOC), triheptyl citrate (THpC), tri(2-ethylhexyl)citrate (TEHC), triisononyl citrate (TiNC), and tri(2-propylheptyl) citrate (TPHC):
wherein the terephthalate-based material is one or more selected from the group consisting of di(2-ethylhexyl) terephthalate (DEHTP), diisononyl terephthalate (DINTP), diisodecyl terephthalate (DIDTP), di(2-propylheptyl)terephthalate (DPHTP), diamyl terephthalate (DATP), dibutyl terephthalate (DBTP), butylisononyl terephthalate (BINTP), butyl(2-ethylhexyl) terephthalate (BEHTP), amylisononyl terephthalate (AINTP), isononyl(2-propylheptyl) terephthalate (INPHTP), amyl(2-propylheptyl) terephthalate (APHTP), amyl(2-ethylhexyl) terephthalate (AEHTP), (2-ethylhexyl)(2-propylheptyl) terephthalate (EHPHTP) and (2-ethylhexyl)isononyl terephthalate (EHINTP), and
wherein the dibenzoate-based compound is triethylene glycol dibenzoate (TEGDB) or dipropylene glycol dibenzoate (DPGDB), and TEGDB or DPGDB is the only the dibenzoate-based compound included in the plasticizer composition.

* * * * *